(12) United States Patent
Zielinski (10) Patent No.: US 11,210,742 B2
(45) Date of Patent: *Dec. 28, 2021

(54) ACCUMULATOR SYSTEMS AND METHODS

(71) Applicant: UnitedHealth Group Incorporated, Minnetonka, MN (US)

(72) Inventor: Thomas E. Zielinski, New Vernon, NJ (US)

(73) Assignee: UNITEDHEALTH GROUP INCORPORATED, Minnetonka, MN (US)

( * ) Notice: Subject to any disclaimer, the term of this patent is extended or adjusted under 35 U.S.C. 154(b) by 143 days.

This patent is subject to a terminal disclaimer.

(21) Appl. No.: 16/751,654

(22) Filed: Jan. 24, 2020

(65) Prior Publication Data

US 2020/0160988 A1     May 21, 2020

Related U.S. Application Data (63) Continuation of application No. 16/055,937, filed on Aug. 6, 2018, now Pat. No. 10,566,086, which is a continuation of application No. 14/281,320, filed on May 19, 2014, now Pat. No. 10,042,982.

(51) Int. Cl.
   *G06Q 40/08*          (2012.01)
   *G16H 40/20*          (2018.01)

(52) U.S. Cl.
   CPC ............. *G06Q 40/08* (2013.01); *G16H 40/20* (2018.01)

(58) Field of Classification Search
   CPC ........ G06Q 50/22; G06Q 40/08; G06Q 40/00; G06Q 10/10; G06Q 50/24; G06Q 30/04; G06F 19/328; G16H 10/60; G16H 40/20
See application file for complete search history.

(56) References Cited

U.S. PATENT DOCUMENTS

| | | |
|---|---|---|
| 7,624,026 B2 | 11/2009 | DiPiero et al. |
| 7,769,606 B2 | 8/2010 | Boone et al. |
| 7,783,501 B2 | 8/2010 | Slen et al. |
| 8,099,302 B2 | 1/2012 | Chapman et al. |
| 8,296,164 B2 | 10/2012 | Oscar et al. |
| 8,494,876 B2 | 7/2013 | Chapman et al. |

(Continued)

OTHER PUBLICATIONS https://money.stackexchange.com/questions/21284/out-of-pocket-maximum-and-health-insurance-plan-terminology-calculation, Mar. 26, 2013 (Year: 2013).*

(Continued)

*Primary Examiner* — Joseph D Burgess
(74) *Attorney, Agent, or Firm* — Dorsey & Whitney LLP (57) ABSTRACT

Healthcare costs accumulated across a plurality of claims systems are managed using a centralized accumulator, which receives cost accumulator data for adjudicated claims from multiple sending claim systems. An accumulator record type is identified from the cost accumulator data and used to generate a cross-reference record. The record type includes an adjudicated claim. A routing message is generated for at least one receiving claim system according to the identified accumulator record type, the cost accumulator data received from the sending claim system, and an identity of the at least one receiving claim system. In response to sending the routing message to the receiving claim system, an acknowledgement is received, which is used to update the cross-reference record by the processor.

20 Claims, 8 Drawing Sheets

(56) References Cited

U.S. PATENT DOCUMENTS

| | | |
|---|---|---|
| 2002/0103680 A1 | 8/2002 | Newman |
| 2006/0149595 A1 | 7/2006 | Williams et al. |
| 2007/0271119 A1* | 11/2007 | Boerger ............... G06F 19/328 |
| | | 705/2 |
| 2008/0004910 A1 | 1/2008 | Higgins |
| 2008/0033750 A1 | 2/2008 | Burriss et al. |
| 2008/0156868 A1 | 7/2008 | Slen et al. |
| 2011/0010189 A1 | 1/2011 | Dean et al. |
| 2012/0271776 A1 | 10/2012 | DiPiero et al. |
| 2013/0054261 A1 | 2/2013 | Dufour |
| 2013/0110539 A1 | 5/2013 | Sohr et al. |
| 2013/0246094 A1 | 9/2013 | Cruise |
| 2018/0350463 A1 | 12/2018 | Zielinski |

OTHER PUBLICATIONS

"Oracle Health Insurance Benefit Accumulator Management", Oracle Insurance 2013. (2 pages).
"XpandACC: Real-time Solution for Shared Benefits Accumulators (Medical, Pharmacy, Mental, Vision, and Dental).", Acero Health Technologies 2013, downloaded Oct. 15, 2014 http://www.acerohealthtechnologies.com/products/xpandacc. (3 pages).
Money.Stackexhange, "https://money.stackexchange.com/questions/21284/out-of-pocket-maximum-and-health-insuracne-plan", Mar. 23, 2013.

* cited by examiner

Table 372:

| CLAIM SYSTEM ID | CLAIM SYSTEM TYPE ROUTING TO | 377 ACCUMULATOR TYPE | 377 BENEFIT TYPE | 378 ACCUMULATOR TYPE | 378 BENEFIT TYPE | 379 ACCUMULATOR TYPE | 379 BENEFIT TYPE | 380 ACCUMULATOR TYPE | 380 BENEFIT TYPE |
|---|---|---|---|---|---|---|---|---|---|
| 1000 | DN | DED | - | OOP | - | - | - | OOP | 0 |
| 2000 | VS | DED | - | OOP | - | DED | 0 | OOP | 0 |
| 3000 | RX | DED | - | OOP | - | DED | 0 | | |
| 4000 | BH | DED | - | OOP | - | DED | 0 | | |

Table 386:

| ACCUMULATOR START DATE | ACCUMULATOR END DATE | CLAIM ACCUMULATOR TYPE CODE | CLAIM BENEFIT TYPE CODE | AMOUNT APPLIED TO INDIVIDUAL | INDIVIDUAL PLAN LIMIT | YTD APPLIED TO INDIVIDUAL |
|---|---|---|---|---|---|---|
| 1/1/2013 | 12/31/2013 | DED | - | 200 | 2000 | 1200 |
| 1/1/2013 | 12/31/2013 | OOP | - | 200 | 3000 | 1200 |
| 1/1/2013 | 12/31/2013 | DED | 0 | 200 | 4000 | 1200 |
| 1/1/2013 | 12/31/2013 | OOP | 0 | 200 | 6000 | 1200 |

ACCUMULATOR SYSTEMS AND METHODS

CROSS-REFERENCE TO RELATED APPLICATION(S)

This application is a continuation of U.S. application Ser. No. 16/055,937, filed Aug. 6, 2018, issued Feb. 18, 2020, as U.S. Pat. No. 10,566,086, which is a continuation of U.S. application Ser. No. 14/281,320, filed May 19, 2014, issued Aug. 7, 2018, as U.S. Pat. No. 10,042,982, each of which is incorporated by reference.

TECHNICAL FIELD

Implementations relate to computer systems, methods and computer readable media for managing health care costs, and more particularly, to managing accumulator updates across a number of systems sharing member cost accumulators.

BACKGROUND

Many health insurance plans provide shared deductible and out-of-pocket limits that cover different types of benefits. For instance, a medical plan may share deductible and out-of-pocket expenses with the pharmacy and behavioral benefit plans. All of a member's medical, pharmacy and behavioral claims would be applied against one deductible plan limit and one out-of-pocket limit, instead of three separate sets of accumulators (i.e. deductible and out-of-pocket limits) for each benefit type.

Often different benefit types are administered by different claim adjudication systems, e.g., three separate systems to handle medical, pharmacy and behavioral claims. In order for these systems to properly apply a claim against a member's shared deductible and out-of-pocket limits, they each must be aware of the claims the other systems may have adjudicated for that member and the cost share amount applied to the shared accumulators. In a simple scenario, with three systems administering three different benefit types, medical, pharmacy and behavioral, there are numerous interfaces and exchanges that are needed. For instance, the medical system sends accumulator updates to the pharmacy and behavioral systems for medical claims; and pharmacy and behavioral systems need to send the medical system accumulator updates for a pharmacy claim or behavioral claim, respectively.

Further, for complex health care systems operating multiple medical systems, specialty benefit systems and external delegated entities, the number of interfaces needed to support the accumulator update process grows dramatically. Moreover, these interfaces are typically developed as "one-offs" where each interface has its own requirements and specifications. Consequently, there is a great deal of overlap and costs to maintaining and adding new interfaces. This problem is exacerbated by the advent of health care reform, whereby commercial medical plans need to include pharmacy, behavioral, physical health, dental and vision benefits as part of the core medical benefits with one set of shared accumulators.

Currently these interfaces are handled by each system receiving and sending file based updates to the other system. Typically these updates are grouped together based on a specified time interval and submitted in batches. This results in timing issues when a member submits multiple claims for different benefit types within a short duration of time. For instance, a member submits a $200 medical claim and a $100 pharmacy claim on the same day. Also assume the member's current out-of-pocket balance is $1800 and the maximum is set at $2000. The medical system processes the claim applying the $200 toward the out-of-pocket. The member's out-of-pocket maximum has now been reached but the medical system does not send the update to the pharmacy system until several days later as part of a batch process it runs. Meanwhile, the pharmacy system receives the $100 claim and also applies it toward the member's out-of-pocket since it is not aware of the $200 medical claim that was already processed. As a result the member has been charged an additional $100 when in fact the out-of-pocket maximum has already been reached. The member is dissatisfied and reports the issue, requiring the insurance company to investigate the matter, reconcile claims and correct the problem. Consequently, there is a need to provide a way to manage accumulator updates between multiple systems.

SUMMARY

The present disclosure provides a centralized accumulator for managing the exchange and acknowledgement of accumulator updates between multiple systems, such as claim adjudication engines, utilizing shared accumulators.

According to one implementation, a computer-implemented method manages healthcare costs accumulated across a plurality of claims systems. The method involves using a computer processor that executes the steps to manage such accumulated costs. The processor receives cost accumulator data for a plurality of adjudicated claims from a plurality of sending claim systems. For instance, the cost accumulator data includes an accumulated cost for healthcare services received by the member over a selected period of time. The processor identifies an accumulator record type from the cost accumulator data. These record types include an adjudicated claim, an initial accumulator record, an update accumulator record and an acknowledgement accumulator record. A cross-reference record is generated by the processor for the cost accumulator data according to the accumulator data type. A routing message is generated by the processor for at least one receiving claim system different from the sending claim system, and in generating the message, the processor uses a) the identified accumulator record type, b) the cost accumulator data received from the sending claim system, and c) an identity of the at least one receiving claim system. The routing message is routed to the at least one receiving claim system by the processor, and at least one of an initial, an update or an acknowledgement accumulator record is received by the processor from the at least one receiving claim system, which is used to update the cross-reference record by the processor.

According to another implementation, a computer system for managing healthcare costs accumulated across a plurality of claims systems uses one or more computer processors to manage such costs. The processors receive adjudicated claim data for a plurality of adjudicated claims from a plurality of sending claim systems. Cost accumulator records are generated by the processors using the adjudicated claim data for each of the plurality of members. These records may include, for instance, an accumulation of healthcare costs incurred over a pre-defined time period. For each of the plurality of cost accumulator records, accumulated costs are separated into deductible cost accumulator records and out-of-pocket cost accumulator records. In addition, for each of the deductible cost accumulator records and the out-of-pocket cost accumulator records, the accumulated costs incurred within a network for a health plan of a member are separated from accumulated costs incurred outside of the network. Consequently, four cost accumulator types are generated including a deductible in-network cost accumulator, a deductible out-of-network cost accumulator, an out-of-pocket in-network cost accumulator, and an out-of-pocket out-of-network cost accumulator. A plurality of these cost accumulator types are routed to a plurality of receiving claim systems, which share cost accumulators at least one of the sending claim systems, and an acknowledgement from the receiving claim systems is received by the processors. Such an acknowledgement includes a record of the receiving claim system's cost accumulator records for the plurality of the cost accumulator types routed.

In yet another implementation, a computer-implemented method for managing healthcare costs accumulated across a plurality of claims systems involves using a computer processor to manage these costs. The computer processor receives claim data for at least one claim for a member of a health plan. The claim data is received from one of a first medical or non-medical claim system and includes accumulated cost of services received by the member under the health plan over a pre-defined period of time. An accumulator record is generated by the processor using the accumulated cost of services received, and the processor routes the accumulator record to another of the medical or non-medical claim system having an accumulator shared with the first medical or non-medical claim system. An acknowledgement accumulator record is received by the processor from the another claim system, and the acknowledgement accumulator record includes the another claim system's accumulated cost of services for the member under the health plan.

It will be understood the operations may be performed by one processor or multiple processors operating in concert, and the one or more processors may be implemented using one or more servers.

DETAILED DESCRIPTION

Overview

A centralized accumulator system manages cost accumulator updates exchanged among multiple claim adjudication engines that share cost accumulators. Claim adjudication engines may communicate directly with the centralized accumulator instead of with each other. The centralized accumulator system may serve as a hub for shared accumulators that require updating across multiple claim adjudication engines, may manage the inter-system exchange of records, and may manage the local storage of such records.

Generally, cost accumulators applied to a member's health plan include four different types based on the combination of one cost accumulator and one benefit type. These include: 1) a deductible in-network accumulator, 2) a deductible out-of-network accumulator, 3) an out-of-pocket in-network deductible, and/or 4) an out-of-pocket out-of-network accumulator. Values associated with these accumulators may include amounts applied, the current balances and annual maximums. Such accumulator values may be present for a member including individuals and a family under the member's plan. Accumulator values may be calculated by a medical claim adjudication engine. That is, where a claim is derived from a non-medical claim adjudication engine (e.g., a dental, vision, behavioral, physical health or pharmacy claim adjudication engine), the claim may be routed to a medical claim adjudication engine for calculating benefits and accumulator values for members, and the accumulator record may be provided to the centralized accumulator for management of the accumulator updates across multiple claim adjudication engines.

Management of accumulators by the centralized accumulator system involves identifying various types of accumulator records, validation and routing the records to those claim adjudication engines sharing cost accumulators for a member. Records supplied by source claim adjudication engines may be stored by the centralized accumulator and may be used to generate routing records that are transmitted to partnering claim adjudication engines based on cross-reference tables (e.g., routing tables) maintained by the centralized accumulator.

To support the processes of the centralized accumulator, four types of accumulator records may be sent to and/or generated by the centralized accumulator depending on the phase of flow the claim is in and the content. The four accumulator record types managed by the centralized accumulator include adjudicated claims (ADJCLM), initial accumulator records (ACCINT), update accumulator records (ACCUPD) and acknowledgement accumulator records (ACCACK). Each of the participating claim adjudication engines may tag the records when it sends a record to the centralized accumulator. As described, the centralized accumulator may modify the tag when routing the record to partnering claim adjudication engines.

The ADJCLM accumulator record type represents a post-adjudicated claim record, which includes the amounts applied to each accumulator, the current balances of each accumulator and annual maximums for each accumulator at the time it was adjudicated. If any of the accumulators are shared, the record identifies the claim adjudication engines where the accumulator information needs to be routed. Before the centralized accumulator routes the adjudicated claim record, it creates a subset of the record in the form of an accumulator record. For instance, the centralized accumulator may tag the subset record as ACCINT if the record is to be sent to a medical claim adjudication engine (since it represents an initial accumulator record for a medical system) or the subset record may be tagged as ACCUPD if the record is to be sent to specialty benefit claim adjudication engines (e.g. vision or dental).

As mentioned, the ACCINT accumulator record type represents a subset of a post-adjudicated claim record, but contains the same accumulator content as an ADJCLM record. Medical claim adjudication engines use ACCINT records when a pharmacy or behavioral claim is sent to the centralized accumulator. Additionally, some medical claim adjudication engines may use this record type for a medical claim instead of sending a full post-adjudicated claim record (ADJCLM). The centralized accumulator may route the entire content of the record, for instance, due to this record being formatted as an accumulator record. In some implementations, before routing, the record's tag may be changed to ACCUPD when the record for a recipient represents an accumulator update.

The ACCUPD accumulator record type may be sent by a medical claim adjudication engine to the centralized accumulator after processing an accumulator record received from the centralized accumulator for a specialty benefit claim. In addition or alternatively, the ACCUPD record may be sent by a centralized accumulator to non-medical claim adjudication engines. The ACCUPD record may contain the amounts applied to each accumulator, the current balances of each accumulator and annual maximums for each accumulator as it is currently reflected in the medical claim adjudication engine. If any of the accumulators are shared, the record identifies the claim adjudication engines where the accumulator amounts need to be routed. The centralized accumulator routes the content of the ACCUPD record as well as additional data from the original ADJCLM or ACCINT record. If the centralized accumulator sends the record back to the source of the claim, the record's tag is changed to ACCACK, or alternatively, the same ACCUPD tag is used.

The ACCACK accumulator record type is sent by a specialty benefit system after receiving an ACCUPD or ACCINT record from the medical system via the centralized accumulator. The ACCACK record may contain the amounts applied to each accumulator, the current balances of each accumulator and annual maximums for each accumulator as it is currently reflected in the medical system. If the medical system requires acknowledgements, the centralized accumulator routes the content of the record as well as additional data from the original ADJCLM or ACCINT record. The same ACCACK tag may be kept. In some cases, specialty benefit systems such as dental and vision claim adjudication engines may require the ACCACK record where these systems initiated the transaction, or where all claim adjudication engines initiating the transaction are to receive an ACCACK record. Additionally, an ACCACK record can also be used by the medical claim adjudication engine to indicate that an overage situation or other type of problem exists with the record received. In this case, an error code is sent by the medical claim adjudication engine to the centralized accumulator where the record is routed back to the original claim adjudication engine.

By tracking cost accumulators derived from post-adjudicated claim data based, in part, on accumulator record type, the shared accumulator system is able to track the flow of accumulator data within the cost accumulator system and across multiple claim adjudication engines. The cost accumulator system additionally tracks cost accumulator data based, in part, on accumulator record sub-type, which enables the system identify new accumulator records, replacements, deletions and so on. This enables the centralized accumulator system to generate detailed reports, track discrepancies across systems, and make corrections or replacements to accumulator records, which may be transmitted to partnering systems, when applicable.

System Architecture

Figure 1:
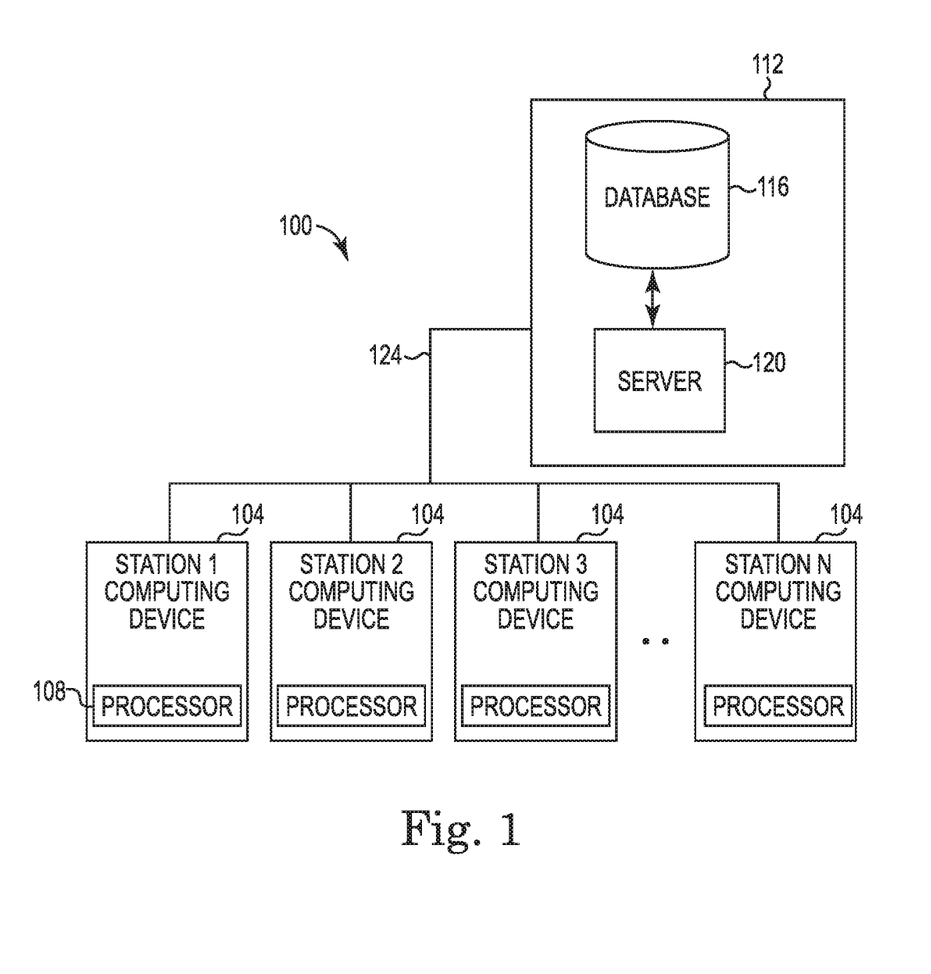
FIG. 1 is high-level block diagram of an example system architecture in accordance with the present disclosure.

FIG. 1 is high-level block diagram of an example system architecture in accordance with embodiments discussed herein. The example system is generally identified with reference numeral 100. The system 100 provides a centralized source for managing the exchange accumulator data among multiple claim adjudication engines utilizing shared accumulators and has particular, but not exclusive application to payers administering insurance e.g., medical, dental, vision, behavioral, physical health and pharmacy insurance. The payer environment or other environment in which the system 100 operates typically contains one or more stations that are staffed with personnel who are provided with one or more station computing devices 104. For instance, payers operating claim adjudication engines may house computing devices 104 for operation by specialists trained to receive and adjudicate claims and to transmit accumulator records to the centralized accumulator 112.

The computing device 104 may include memory and one or more processors 108 that support the accumulator update functions of the system 100 as well as the claim adjudication engine functionalities managed by the medical, dental, vision, pharmacy, behavioral or physical health claim adjudication systems. In one respect, the processor 108 may be configured to run computer executable code that manages the flow of data to and from other system components 100. The processor 108 may additionally be configured to run applications that execute higher level data processing functions. Thus, the processor 108 may be provided in association with a computer readable storage medium that stores processor executable code. The processor executable code may be stored on a long-term basis in a non-volatile memory portion of the computer readable storage medium. The processor executable code may also be loaded into a volatile memory portion of the computer readable storage medium from another location such as from across a network 124. In addition or alternatively, the one or more processors 108 may be configured as a server or a collection of servers. Further, the memory of the computing devices 104 may include one or more databases.

The system 100 generally includes a centralized accumulator 112 that causes accumulators to be updated across the system using capabilities of one or more data processing applications. Such capabilities may include logging, validation and storing accumulator records; partner system routing; logging transmission of accumulator events and report generation. Data processing applications, or portions thereof, may execute on one or more severs 120 of the centralized accumulator 112, and in some instances, may execute on the processor 108 associated with the computing device 104. The centralized accumulator 112 may additionally include one or more databases 116 that stores accumulator data. By way of example, accumulator data may include electronic accumulator records such as full claim records or partial claim records with data elements needed to support the accumulator exchange process, cross-reference tables (e.g., routing and reference tables), routing records, copies thereof, and so on.

Figure 2:
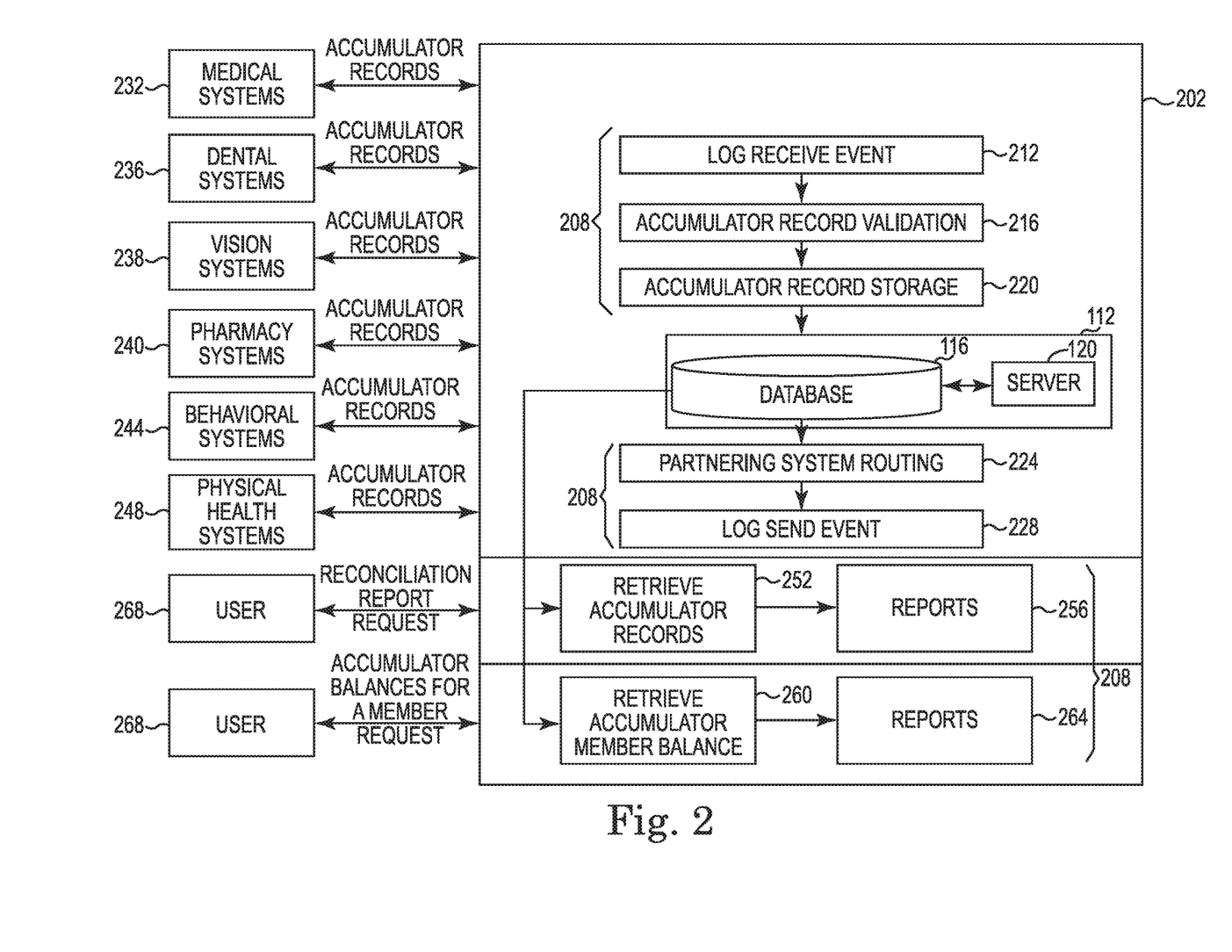
FIG. 2 is a schematic illustration of an example data processing application in accordance with the present disclosure.

FIG. 2 is a schematic illustration of an example data processing application 202 in accordance with embodiments discussed herein. The data processing application 202 includes or is in communication with the centralized accumulator 112, which is communicatively coupled to the computing devices 104 associated with the claim adjudication engines. In FIG. 2, the data processing application 202 includes various data processing capabilities 208 that facilitate the centralized accumulator 112 in updating accumulator records across partnering claim adjudication engines. In this regard, the data processing application 202 may be communicatively coupled to, or portions may be integrally operable with, partnering claim adjudication engines such as medical systems 232, dental systems 236, vision systems 238, pharmacy systems 240, behavioral systems 244 and physical health systems 248. For instance, the data processing application 202 may be configured to deploy a common interface to each of the partnering claim adjudication engines to facilitate communications with the centralized accumulator 112. The common interface may require that accumulator record data needed to support the accumulator exchange process be submitted in a pre-defined format. This common interface may replace individual interfaces each claim adjudication engine would otherwise need to develop and maintain.

Turning now to the various capabilities 208 of the data processing application 202, as can be seen in FIG. 2, the data processing application 202 may utilize a log receive event module 212, which may be in communication with the various application services and the centralized accumulator 112. The log receive event module 212 may log key information about post-adjudicated claims or accumulator records when received into the system 100. The records generated by may include an inventory control number assigned by the centralized accumulator 112, a date and time the claim or accumulator record was generated, and an event identification code corresponding to whether the claim or accumulator record received is a received record, a routed record or a completed record. Types of received records may include ADJCLM, ACCINT, ACCUPD or ACCACK and types of routed records may include ACCINT, ACCUPD or ACCACK. Accordingly, the log receive event module 212 causes an event to be logged upon receipt by the system 100, and claim adjudication engines sending such records also logs their own sending events. Consequently, the log receive event module 212 reconciles sending and receiving of accumulator records with partnering claim adjudication engines to ensure no transactions are lost between systems.

The accumulator record validation module 216 may cause records received and logged by the system 100 to be validated. Validation may involve checking for duplicate records; confirming a start date is less than an end date; confirming required fields in the records are complete; and/or confirming the records received are derived from post-adjudicated claims. For post-adjudicated claims (ADJCLM), validation may involve confirming information from the claim is to be routed by confirming routing information complete, and if so, validating the required accumulator fields in the claim. For initial accumulator records (ACCINT), update accumulator records (ACCUPD) or acknowledgement accumulator records (ACCACK), validation may involve confirming accumulator values are present. For update or acknowledgement records, validation may involve confirming a record is present in a cross-reference table (e.g., claim information table) that relates to the claim or accumulator record. Other fields in a record that may be validated include claim record type (e.g., claim or accumulator record), claim system identification (e.g., originating claim system identification), process flow key (e.g., ADJCLM, ACCINT, ACCACK, ACCUPD), responding/sending system identification, medical claim identification number, accumulator record identification number, accumulator record sub-type, (e.g., update such as original, underpayment, overpayment, void, reissue (001); delete/replace such as a record reprocessed prior to payment (002); or special replacement such as a record resent replacement without negate applied (003)), coverage type code (e.g., pharmacy, medical, behavioral health, vision, dental, or physical health), accumulator start date, accumulator end date, accumulator network type (e.g., in-network provider, out-of-network provider or out-of-network provider adjudicated as in-network provider), accumulator type (e.g., deductible or out-of-pocket), accumulator benefit type (e.g., in-network or out-of-network), accumulator applied amount (individual and family) accumulator plan amount (individual and family), accumulator year-to-date amount (individual and family), and/or whether an accumulator amount applies across accumulators.

The accumulator record storage module 220 may cause the record, or portions thereof, to be stored in one or more cross-reference tables managed by the one or more databases 116. For instance, a claim information table may store records for each claim and initial accumulator record. A names and addresses table may store, for each claim information record in the claim information table, one record for a subscriber and one record for a patient. A claim lines table may store claim lines-related data for each claim information record in the claim information table. A line accumulator values table, when applicable, may store accumulator values for each claim lines record in the claim lines table. An accumulator header table may store one record for each claim, initial accumulator record, accumulator update record, and accumulator acknowledgement record received. An accumulator values table may store accumulator values for each record (e.g., claim, initial accumulator record, accumulator update record, and accumulator acknowledgement record) in the accumulator header table, including one record for each combination of accumulator type (deductible or out-of-pocket) and benefit type (in-network or out-of-network) within a given accumulator period. An accumulator routing table, when applicable, may store routing information for each accumulator header record in the accumulator header table, one record for each combination of system where routing is to occur, accumulator type (deductible or out-of-pocket) and benefit type (in-network or out-of-network). Further, reference tables may be used to convert accumulator record information into a routable format.

The partnering system routing module 224 may cause shared accumulator records to be routed to partnering systems for updating accumulator records of the partnering systems. This enables the centralized accumulator 112 to serve as a central hub for the exchange of records for all partnering systems. Using the partnering system module 224, the partnering systems are identified, for instance, using information from the accumulator routing table, and routing records are generated and routed to the systems sharing a cost accumulator for a member. Routing may be based on instructions provided by the sending system from which the claim or accumulator record is derived. In addition or alternatively, routing may be based on instructions provided by a medical claims system. In particular, such instructions may identify partnering systems sharing a member's cost accumulator.

The log send event module 228 may log accumulator and/or routing records generated, log those that have errors, and log those that were successfully sent to destination claim adjudication engines, e.g., medical systems 232, dental systems 236, vision systems 238, pharmacy systems 240, behavioral systems 244 and physical health systems 248.

The retrieve accumulator records module 252, with the reports module 256, may cause member accumulator records to be retrieved and reports based on the retrieved information to be generated. In addition, the retrieve accumulator member balance module 260 and the reports module 264 may cause member accumulator balances to be retrieved and reports generated based thereon. Such reports may be generated in response to an inquiry by a user 268. For instance, the modules 256, 264 may generate reports for use in reconciling out of balance situations that may occur between partnering systems.

Methods of Updating Accumulators

Figure 3A:
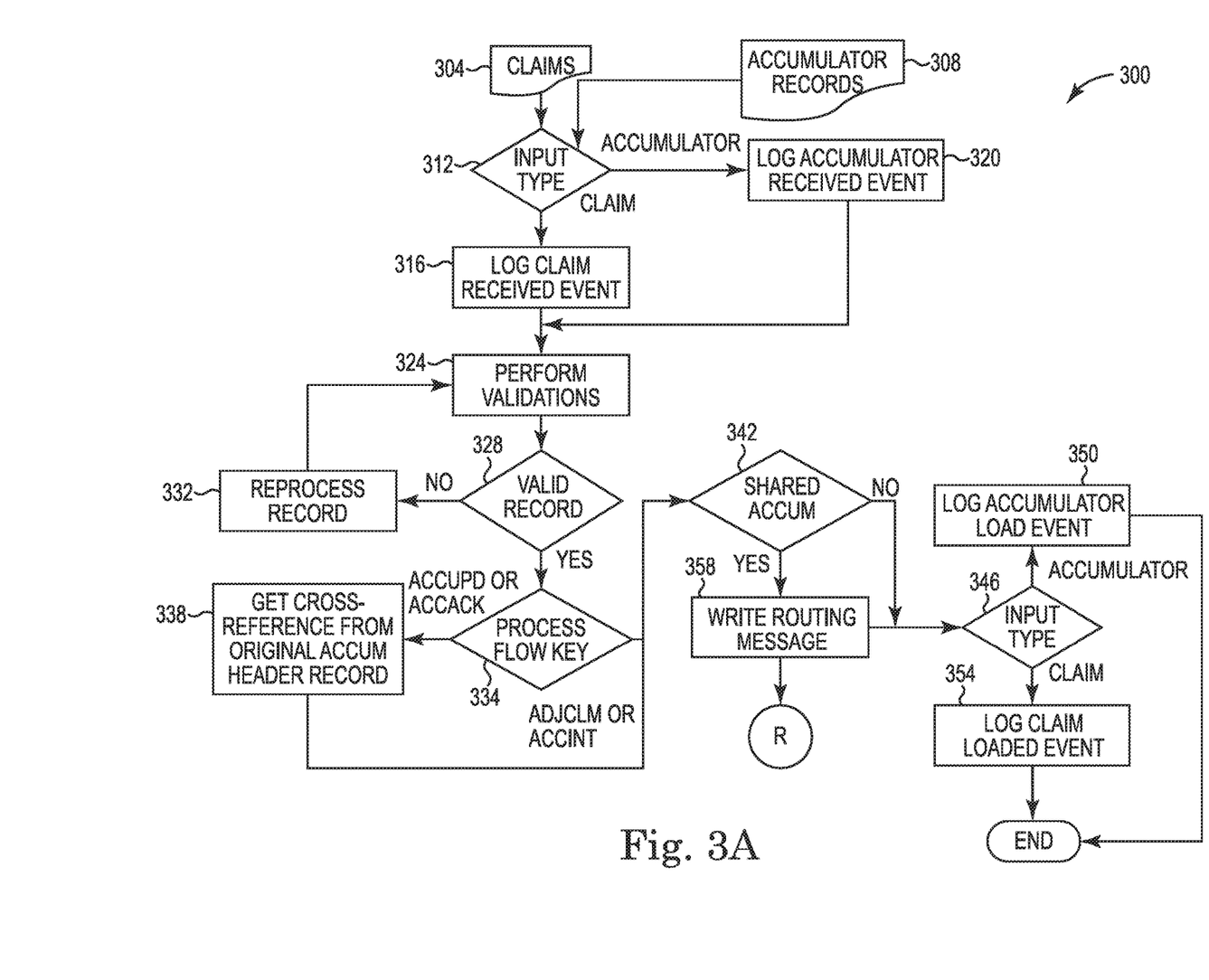
FIG. 3A is a flow diagram of a method of updating accumulators according to the present disclosure.

Turning to FIG. 3A, this figure is a flow diagram of a method 300 of updating accumulators according to the present disclosure. The steps of FIG. 3A may be executed using the system of FIG. 1, and may additionally or alternatively be implemented using the data processing application 202 of FIG. 2. Method 300 begins by claim 304, accumulator records 308, or both, being received from a claims adjudication engine, and determining the record type at decision box 312. The record may be a claim (ADJCLM) or an accumulator record, and the accumulator record may be one of three types: an initial accumulator record (ACCINT), an update accumulator record (ACCUPD) or an acknowledgement accumulator record (ACCACK). For an adjudicated claim, the flow proceeds to operation 316 and a claim received event is logged into tables used in connection with updating accumulators. For an accumulator record, the flow proceeds to operation 320 and an accumulator record received event is logged into tables used in connection with updating accumulators. For instance, logged within a claim information table are records of the received claims and initial accumulator records. Each record in the claim information table may additionally be used to generate a corresponding record in a names and addresses table, and this table may include a record for a subscriber and a record for a patient. Claims with records stored in the claim information table may additionally have claim lines stored in a claim lines table; and where applicable, accumulator values from the stored claim lines may be stored in a line accumulator values table. Claims records and initial accumulator records from the claim information table, as well as update accumulator records and acknowledgement accumulator records may additionally be used to generate records in an accumulator header table. For records stored in the accumulator header table, corresponding accumulator values for these records may be stored in an accumulator values table for each combination of accumulator type (deductible or out-of-pocket) and benefit type (in-network or out-of-network) for a pre-defined accumulator period. In addition, where applicable, for records stored in the accumulator header table, routing information for these corresponding records may be stored in an accumulator routing table. The routing information may be stored as one record for each combination of claim adjudication engine to route to, accumulator type and benefit type, described below.

The logged records are validated in operation 324. Validations may differ based on the type of record received as described herein. According to certain implementations, validation may involve the ADJCLM or ACCINT accumulator records received from claim adjudication engines being validated, in part, based on the accumulator record sub-type, e.g., 001, 002 or 003. Although the accumulator record sub-type is numerically identified, the accumulator record sub-type identification may take any form, e.g., alphabetic (including symbols, punctuation and mathematical symbols), numeric, or alphanumeric. For an ACCUPD or ACCACK record, the following validation steps are not required as those records are inserted into the cross-reference tables upon other validation processes, such as those described in connection with FIG. 2 and due to the records being derived from ADJCLM or ACCINT records. Each accumulator record sub-type may represent different types of validations. This is summarized in Table 1:

TABLE 1

| Type | Description | Accumulator record sub-type | Transaction Code | Event Code |
|---|---|---|---|---|
| Original | Original Version of the entire Claim | 001 | 00 | 00 |
| Underpayment: 2 step | Negate original claim | 001 | 74 | 11 |
| | Add new claim | 001 | 00 | 10 |
| Underpayment: Differential | Up-adjust original line(s) | 001 | 00 | 10 |
| Overpayment: 2 step | Negate original claim | 001 | 74 | 11 |
| | Add new claim | 001 | 00 | 10 |
| Overpayment: Differential | Down-adjust original line(s) | 001 | 77 | 10 |
| Void | Negate original claim | 001 | 74 | 11 |
| Reissue | Add new claim | 001 | 87 | 00/10 |
| Delete | Logical Delete | 002 | 98 | 00/10 |
| Replace of Previously sent Claim that has not yet been sent to Check Write | Replace of Previously sent claim | 002 | 00 | 00/10 |
| | | 002 | 74 | 11 |
| | | 002 | 77 | 10 |
| | | 002 | 87 | 00/10 |
| Special Replacement: | Resend ACCUMS, do not negate | 003 | 00 | 00/10 |
| | | 003 | 77 | 10 |
| | | 003 | 87 | 00/10 |

For instance, when processing an inbound record (ADJCLM or ACCINT) that has an accumulator record sub-type of 001 and is an original following a previously sent 1 or 002 replacement of a previously sent claim, the claim ID for the inbound transaction (accumulator record sub-type of 001) must be different from the previously sent accumulator record sub-type 001 or 002 transaction. When processing an inbound record that has an accumulator record sub-type of 002 and is a replacement following a previously sent accumulator record sub-type of 001, the claim ID for the inbound transaction must match the accumulator record sub-type 001 transaction previously sent. When processing an accumulator record sub-type of 002 that is a replacement following a previously sent replacement (an accumulator record sub-type of 002), the claim ID on the inbound transaction must match the transaction that was previously sent.

Generally, validation of ADJCLM and ACCINT inbound records may include validating records by:
  a. identifying and rejecting duplicates,
  b. rejecting records having an illogical processing date and time (e.g., where the date and time of an inbound record precedes the date and time of a previously received record),
  c. identifying a most recent record from a sequence of new records and processing only the most recent record,
  d. identifying situations where a negative record is needed for an inbound 002 replacement and notifying the system and/or claim adjudication engines of the deletion for the record being replaced, and/or e. identifying situations where a record needs to be deleted in the system and/or in the claim adjudication engines.

More particularly, validation of inbound ADJCLM and ACCINT records may involve querying the accumulator header table for the record with the highest processing date and time having a matching claim adjudication system ID and claim ID with the claim adjudication type of ADJCLM or ACCINT. If the inbound record has an accumulator record sub-type of 001, and if no records were retrieved from the query, then the inbound transaction is inserted into the database (e.g., in cross-reference tables) and routing is initiated as appropriate. If the query results in record retrieval of an accumulator record sub-type of 001, then the inbound transaction is rejected as a duplicate. Where the query results in record retrieval of an accumulator record sub-type of 002, and the inbound record has an illogical processing date and time compared to the retrieved record, then the inbound record is rejected or bypassed. Rejected records may appear on error report for claim adjudication engine to address, while for skipped records, no additional action may be needed on the claim adjudication engine's part and the record will not appear on the error report.

For an inbound record having an accumulator record sub-type of 002 that is a logical delete (e.g., the transaction code is 99), similar to above, the accumulator header table may be queried for the record with the highest processing date and time having a matching claim adjudication system ID and claim ID with the claim adjudication type of ADJCLM or ACCINT. If no record is retrieved, then the inbound transaction may be rejected because there is no matching record to logically delete. If the record retrieved from the query has a finalized status, then the inbound transaction may be rejected (e.g., because a finalized claim record cannot be logically deleted). If a record is retrieved that does not have a finalized status, a new record is inserted into the database that is a copy of the record retrieved from the query, fields that are required for negation are negated and the existing record and the new record are deleted. Where applicable, accumulator routing may be performed on the negated record. See list below for fields that need to be negated.

For an inbound record having an accumulator record sub-type of 002 that is a replacement of a previously sent claim (e.g., where the transaction code is 00, 74, 77 or 87), then, similar to above, the accumulator header table may be queried for the record with the highest processing date and time having a matching claim adjudication system ID and claim ID with the claim adjudication type of ADJCLM or ACCINT. If no record is retrieved, then the inbound record is inserted into the database (out of sequence, replacement is being processed before original) and perform routing as applicable. If the record retrieved has a finalized status, then the inbound record may be rejected because, as mentioned, a finalized claim record cannot be replaced. If the record retrieved from the query has an accumulator record sub-type of 001 and the claim processing date and time is greater than the inbound record, then reject the inbound record (the replacement needs to have a processing date and time of greater than the original record).

If the record retrieved from the query has an accumulator record sub-type of 001 and the processing date and time of the original is less than the inbound transaction, then the inbound transaction is inserted into the database, a new record is inserted into the database that is a copy of the record retrieved from the query, fields that are required for negation are negated and set for deletion. Additionally, if applicable, accumulator routing is performed on the negated record.

If the record retrieved from the query has an accumulator record sub-type of 002 and the record has a processing date and time that is equal to the inbound transaction, then the record is rejected (illogical situation). If the record retrieved from the query has an accumulator record sub-type of 002 and the processing date and time is greater than the inbound transaction, then the record is skipped (out of sequence situation). If the record retrieved from the query has an accumulator record sub-type of 002 and the processing date and time is less than the inbound transaction, then the inbound transaction is inserted into the database, a new record is inserted into the database that is a copy of the record retrieved from the query, fields that are required for negation are negated and the record is set for deletion. The original record retrieved is also set for deletion. Additionally, if applicable, accumulator routing is performed on the negated record.

If the inbound record has an accumulator record sub-type of 003 (e.g., where the transaction code is 00, 77 or 87), the accumulator record is a replacement for situations where a claim adjudication engine downstream from the shared accumulator previously rejected a related accumulator record. Because the record sub-type 003 is a replacement for records previously rejected by downstream claim adjudication engines, these engines will not have added the defective record, and as such, a negation of the original record is not performed like in situations where accumulator records having the sub-type of 002 are received for replacement. Specifically, negation is unnecessary since the downstream system rejected the original record. Accordingly, upon receipt of the accumulator record sub-type of 003, similar to above, the accumulator header table may be queried for the record with the highest processing date and time having a matching claim adjudication system ID and claim ID with the claim adjudication type of ADJCLM or ACCINT. If no record is retrieved, the inbound transaction is rejected. For retrieved records, the inbound transaction is inserted into the database and routed to the medical system, and a new record is inserted into the database that is a copy of the record retrieved from the query, except that certain fields may be negated. Unlike the other negate situations, accumulator routing is not performed on the negated record. The retrieved records are set for deletion. In order to adjust year-to-date accumulators, the original individual accumulator amount applied is subtracted from the original individual accumulator year-to-date amount, and the original family accumulator amount applied is subtracted from the original family accumulator year-to-date amount.

Continuing with FIG. 3, the flow proceeds and a determination is made as to whether the validated records are valid in operation 328. Invalid records may be reprocessed in operation 332 and validations performed in operation 324. Otherwise, where a determination is made that the records are valid, the flow proceeds to operation 334 where a process flow key for the record is determined. The process flow key may be one of ADJCLM (post-adjudicated claim), ACCINT (initial accumulator record), ACCUPD (update accumulator record) or ACCACK (acknowledgement accumulator record). For ACCUPD and ACCACK, the flow proceeds to operation 338 where a cross-reference for an original accumulator header record is retrieved from the accumulator header table, which links the update or acknowledgement record to the original claim or initial accumulator record.

The flow proceeds to operation 342 where a determination is made on whether the record contains a shared accumulator value of greater than zero. If not, this means the accumulator record is not shared across multiple claim adjudication engines and the flow proceeds to operation 346, where the input type is determined to be claim or accumulator, and accumulator records are logged as a loaded accumulator event record in operation 350, while claims are logged as a loaded claims event record in operation 354. When the shared accumulator value is greater than zero, this means the record is shared across multiple claim adjudication engines, and the flow proceeds to operation 358 where a routing message for the record is written. The routing message includes key data elements that identify the record to another claim adjudication engine. For instance, the routing message may include an originating claim adjudication engine identification such as an initial vendor control number, claim identification information, date and time the claim was processed, claim version number, record type (e.g., ADJCLM, ACCINT, ACCUPD or ACCACK), accumulator record sub-type (e.g., original, replacement, void, reissue or adjustment), a sending/responding system identification, and the date and time the routing message is stored locally, e.g., in the database 116. The type of record for the routing message may be determined at operation 346, and accumulator records for routing are logged as a loaded accumulator event record in operation 350, while claim records for routing are logged as a loaded claims event record in operation 354. Where a routing message for the record is generated, at R, the method continues to the flow diagram of FIG. 3B.

Figure 3B:
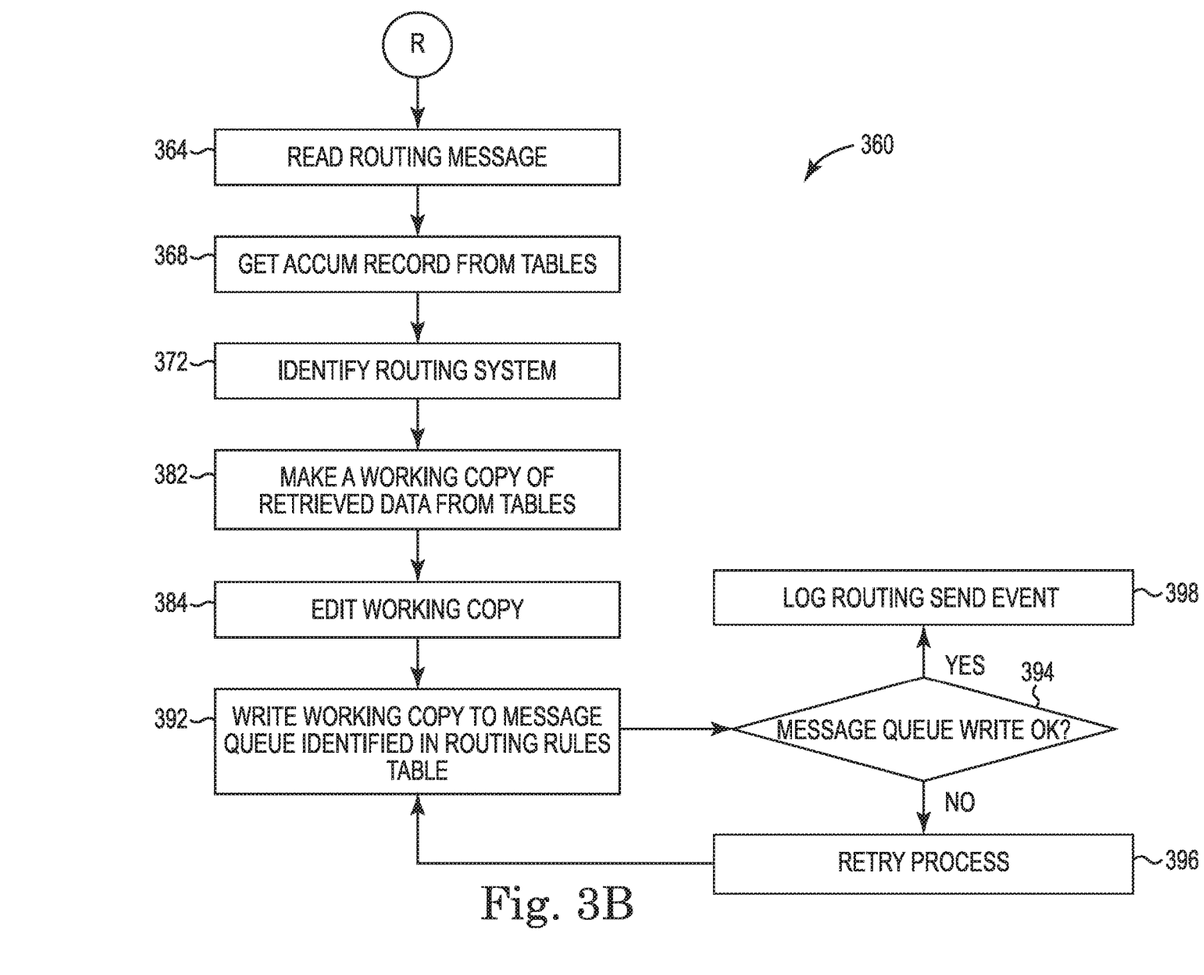
FIG. 3B is a flow diagram of a sub-routine for the method of updating accumulators according to the present disclosure.

FIG. 3B shows a flow diagram of a method 360 of updating accumulators according to the present disclosure. The steps of FIG. 3B may be executed using the system of FIG. 1, and may additionally or alternatively be implemented using the data processing application 202 of FIG. 2. The method starts at R, and the flow proceeds to operation 364 where the routing message generated in operation 358 is read. Using the key data elements from the routing message, the flow proceeds to operation 368 where accumulator records are retrieved from tables. For instance, records may be retrieved from the accumulator header table, accumulator values table, accumulator routing table, claim information table, claim lines table and/or line accumulator values tables. Based on data retrieved from the accumulator routing table, each claim adjudication engine targeted to receive an updated accumulator record has routing records generated. For example, a routing record may be generated for each applicable cost accumulator, accumulator value or both. The routing records for an accumulator record may be written to a routing area such as the routing area table 372 illustrated in FIG. 3C. In this example, records for four different claim adjudication engines are illustrated, dental (DN) 373, vision (VS) 374, prescription (RX) 375, and behavioral health (BH) 376 and are to receive an accumulator record derived from another claim adjudication engine, e.g., a medical claim (MD) adjudication engine. In other examples, one of the claim adjudication engines for routing accumulator records may be the same as the claim adjudication engine from which the claim was derived, such as when an originating claim adjudication engine requires an acknowledgement of an update from a responding claim adjudication engine. Each of the claim adjudication engines may receive up to four different accumulator updates (e.g., cost accumulator types): an update for a deductible amount in-network (DED, I) 377, an update for a deductible amount out-of-network (DED, O) 378, an update for an out-of-pocket in-network (OOP, I) 379, and/or an update for an out-of-pocket out-of-network (OOP, O) 380. For each of the targeted claim adjudication engines, the following operations 372-398 may be executed.

Where multiple modes of communication (e.g., via web services, business-to-business operations, intranet and/or Internet) are responsible for transmitting updates to the various claim adjudication systems, the targeted claim adjudication engine may be evaluated in operation 382 to identify the designated mode of routing.

A working copy of the routing record may be written in operation 382. This operation may facilitate generation of records formatted for the target claim adjudication engine in instances where the content (e.g., accumulator values, routing area, process flow key) of the accumulator record information retrieved from the tables differs from the information that needs to be routed. In this way, the working copy may be modified with information required for the receiving claim adjudication engine, while information required for the system 100 and/or data processing application 202 may remain unchanged.

Figure 3C:
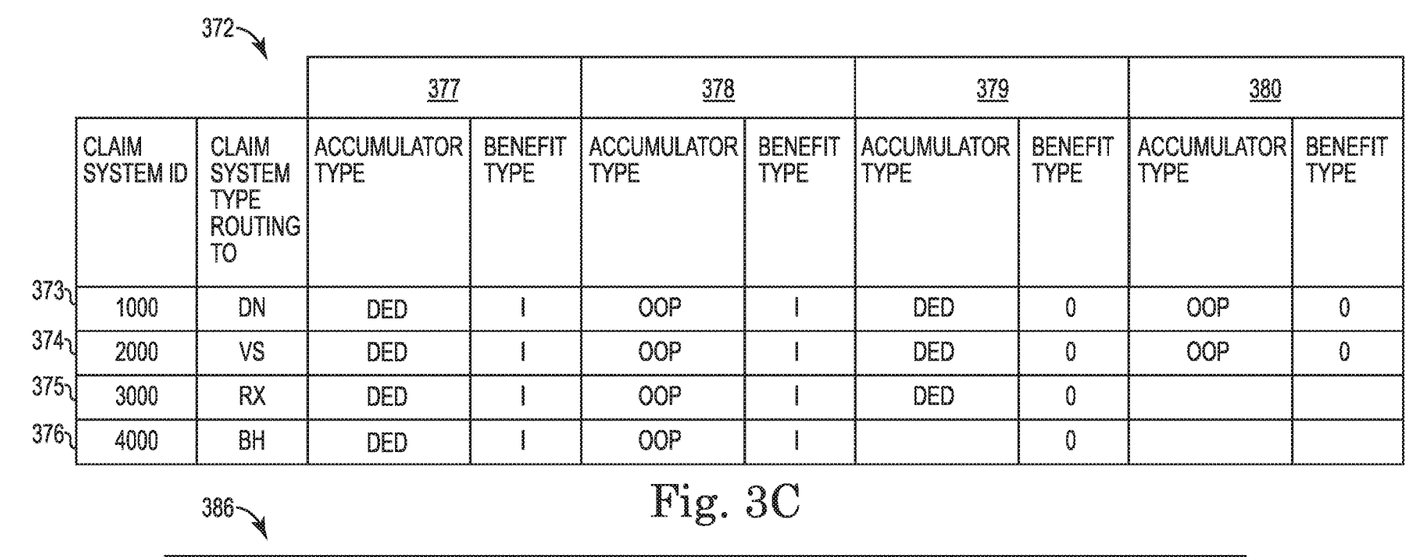
FIG. 3C illustrates a routing area table that may be used in connection with updating cost accumulators according to the present disclosure.
Figure 3D:
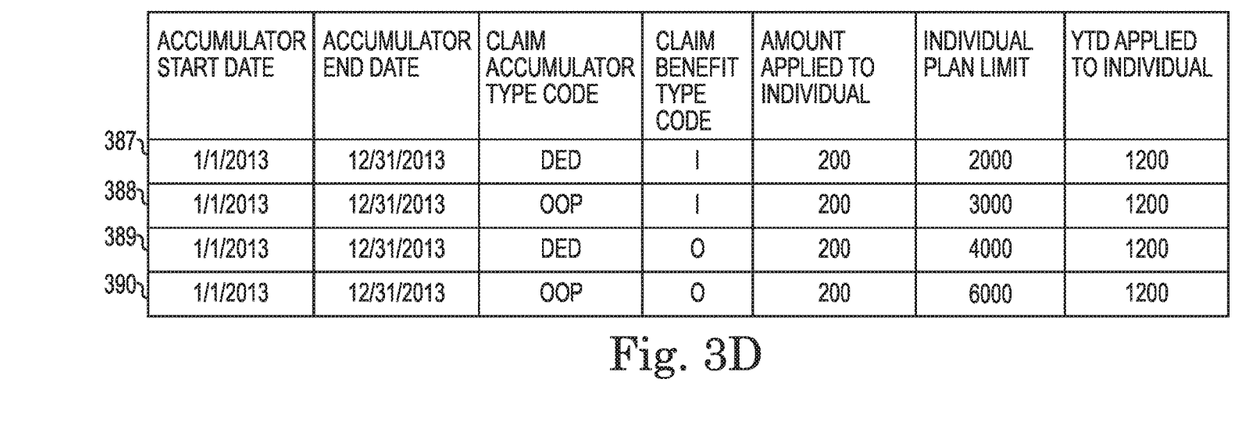
FIG. 3D illustrates a segment of an accumulator values area for an accumulator record that may be used in connection with updating cost accumulators according to the present disclosure.

In operation 384, the working copy may be edited based on the receiving claim adjudication engine. Edits to the working copy may involve, for instance, the addition of accumulator values retrieved in operation 368 that match the accumulator and benefit types (e.g., cost accumulators) identified in the routing area of the accumulator record. For instance, referring to FIG. 3C, the claim adjudication engines may receive between two and four types of accumulator updates (e.g., 377-380), and accumulator values may be written for each update. Where the process flow key equals ACCUPD and the targeted claim adjudication engine is the same as the adjudicating system (e.g., based on the originating claim adjudication engine identification), the process flow key may be changed to ACCACK. This edit may be due to the receipt of an accumulator update record that actually represents an acknowledgement for the original system that submitted the accumulator record (ACCINT). Where the process flow key equals ACCINT, then the process flow key may be updated to ACCUPD. Where the process flow key equals ADJCLM and it is being routed to a medical system, then the process flow key may be changed to ACCINT. For ACCACK records received that are to be routed to a medical system, the working copy may be updated to include a vendor code or other mapping data. The following example describes how the accumulator values and routing areas are edited. For example, shown in FIG. 3D is a sample segment 386 of an accumulator values area for an accumulator record that may be used in connection with updating claim adjudication engines. In FIG. 3D, accumulator value updates 387-390 for a predefined accumulator period are illustrated for the four different accumulator record types 377-380, respectively. In the sample routing area table of FIG. 3C, there are four claim system ID records, and assume the first record 373 for a dental claim adjudication engine is to be processed. In this case all four cost accumulator record types 377-380 and corresponding accumulator value updates 387-390 (e.g., individual amounts, individual plan limits, year-to-date amounts applied to the individual, family amounts, family plan limits, year-to-date amounts applied to the family) would be added to the working copy since all of the benefit and accumulator types match what was identified in the first record of the original routing area. In the routing area of the working copy, only a record corresponding to the dental claim adjudication engine record 373 may be included. Next, assume the fourth record of the routing area table of FIG.

3C, 376 for a behavioral health claim adjudication engine is to be processed. In this case, only two accumulator record types 377-378 and corresponding accumulator value updates 387-388 would be added to the working copy since only those records match the benefit and accumulator types identified in the fourth record of the original routing area. In the routing area of the working copy, only a record corresponding to the behavioral health claim adjudication engine record 376 may be included.

Continuing with FIG. 3B, the flow proceeds to operation 392 where the working copy record is written to a message queue in the routing rules table. The flow proceeds to decision box 394 where a determination is made as to whether the write is successful. If not, a retry process is performed until the write is successful in operation 396. If the write is successful, then a successful route send event is logged at operation 398, and the routing rules table is updated to include a system identification for the claim adjudication engine receiving the accumulator update, and the flow ends.

Figure 4A:
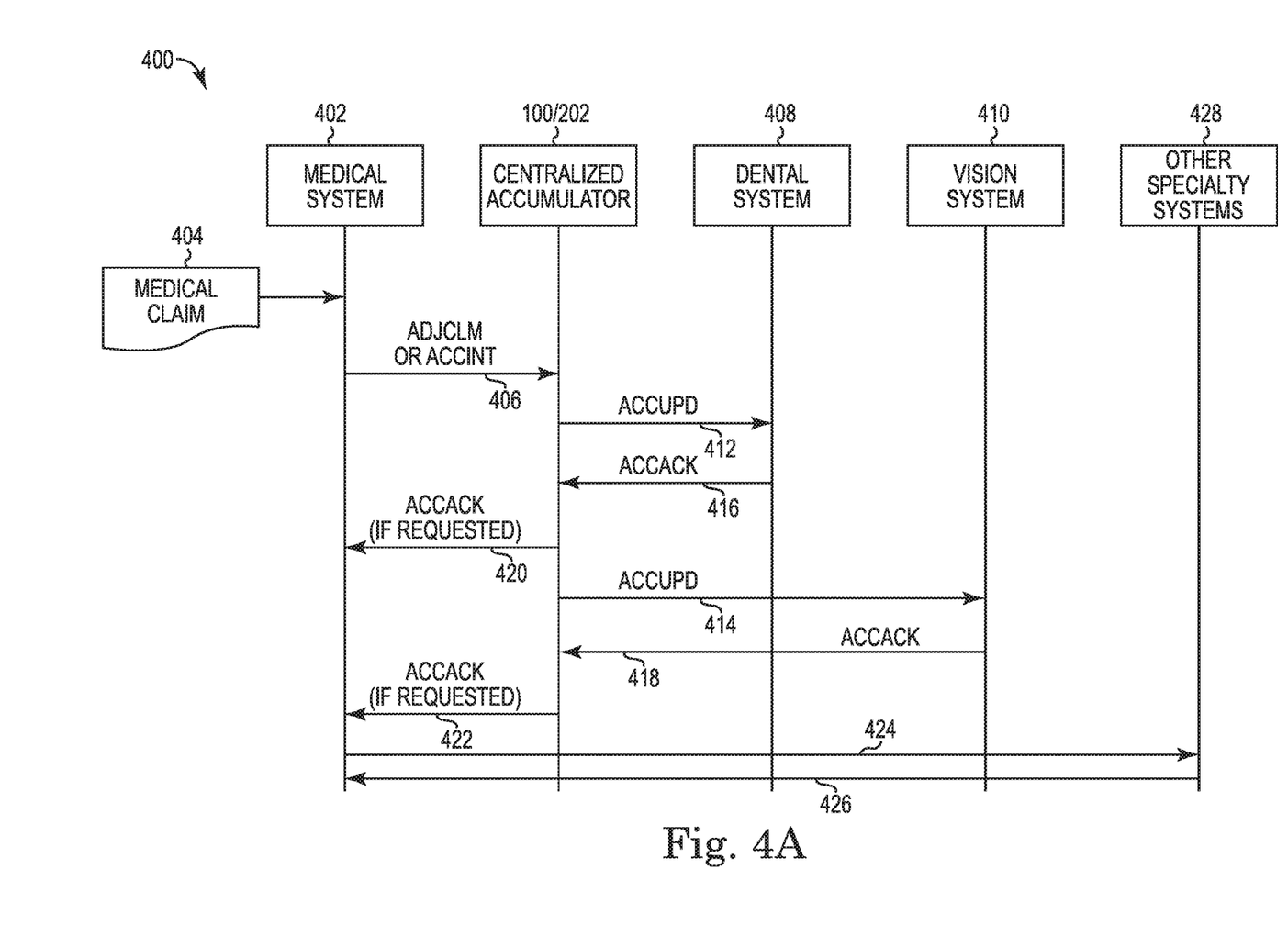
FIG. 4A is a process flow for updating accumulators using medical claim data according to the present disclosure.
Figure 4B:
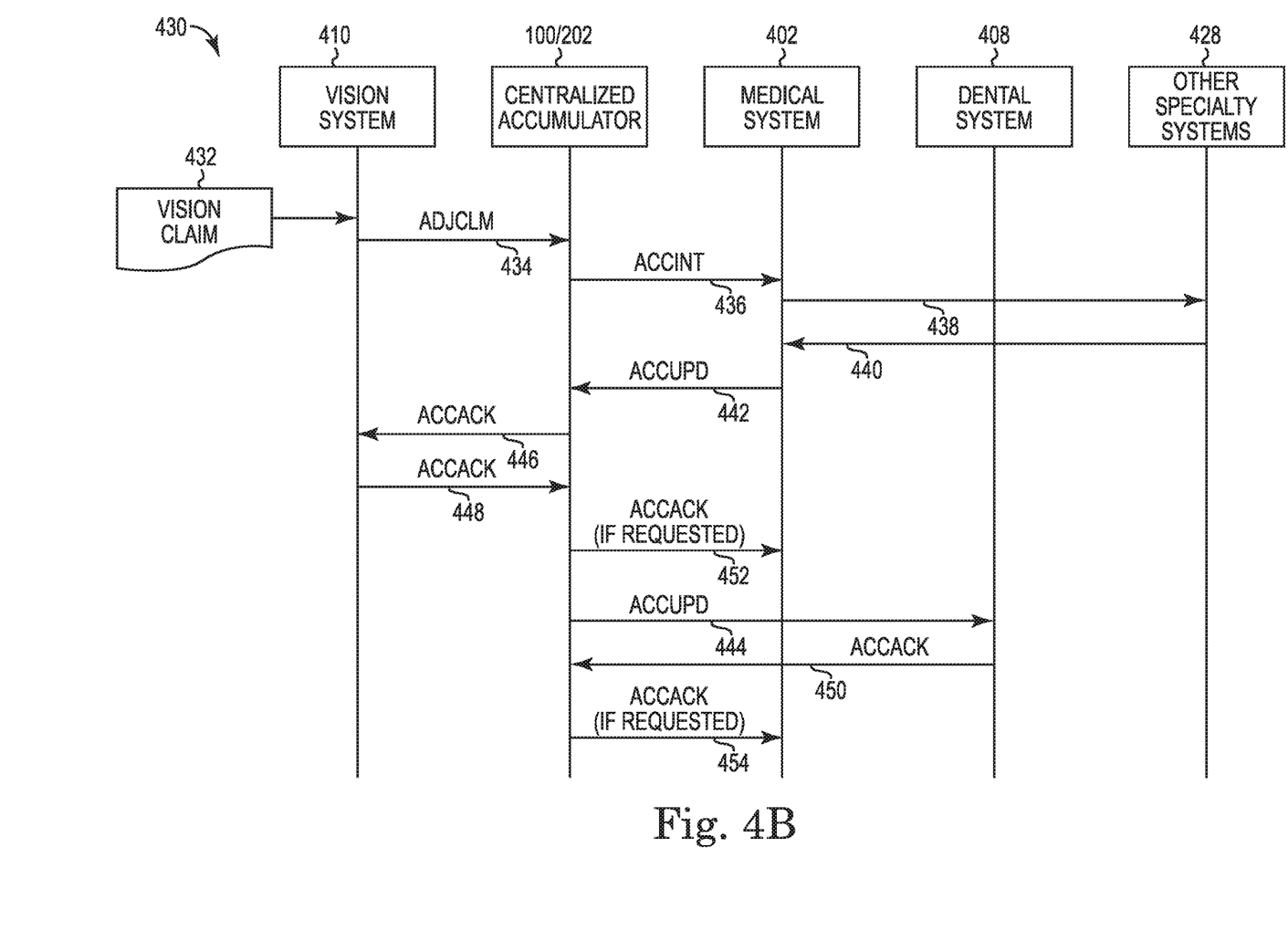
FIG. 4B is a process flow for updating accumulators using vision claim data according to the present disclosure.
Figure 4C:
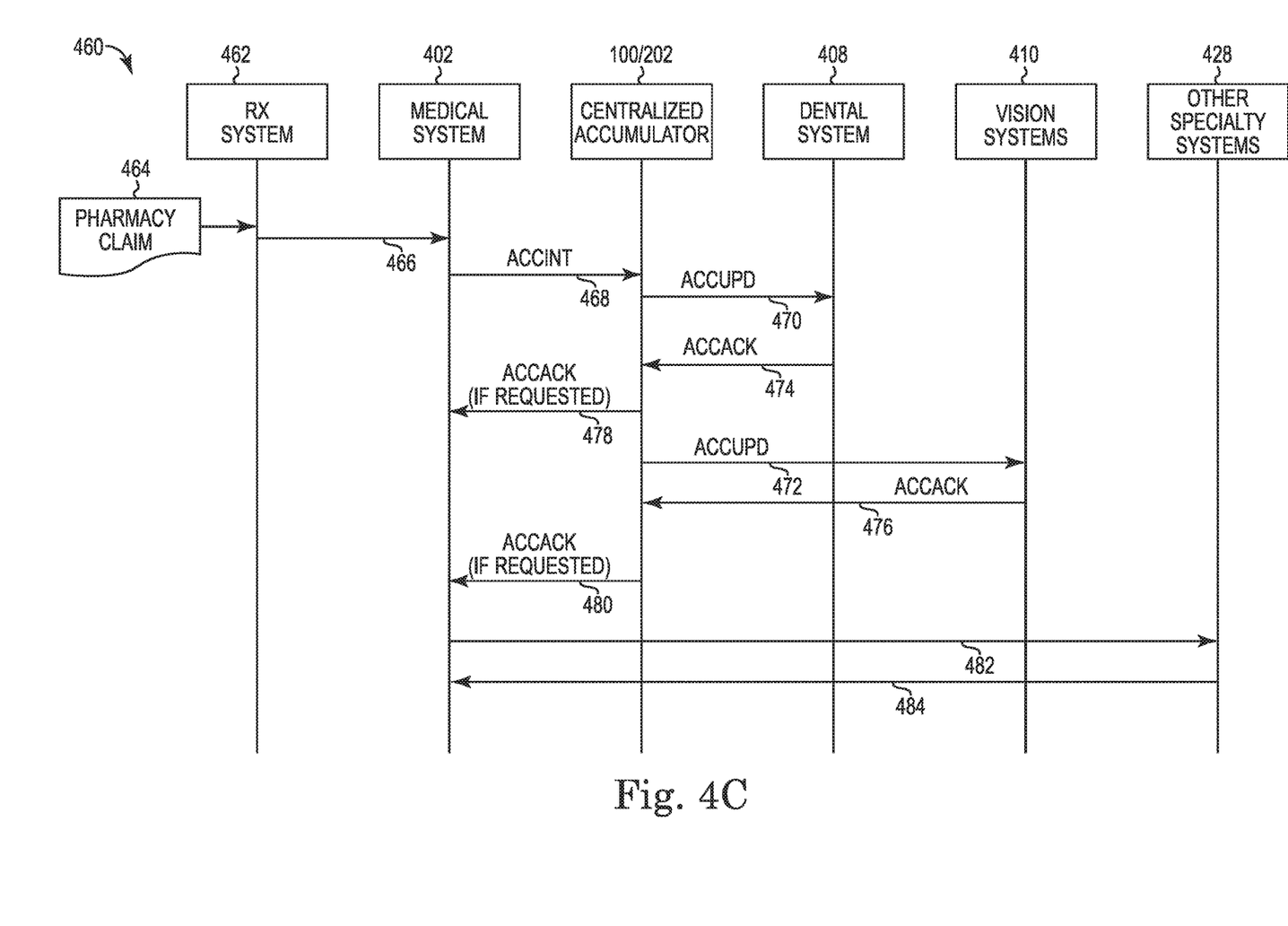
FIG. 4C is a process flow for updating accumulators using pharmacy claim data according to the present disclosure.

In view of the foregoing, accumulator records may be received, stored and routed to various claim adjudication engines. FIGS. 4A-4C provide three basic process flows for the exchange of accumulator records, updates and acknowledgements across medical, specialty benefit claim adjudication systems (e.g., vision and dental) and pharmacy and behavioral claim adjudication systems.

FIG. 4A illustrates a high level process flow 400 for the exchange of claim and accumulator records from a medical claim adjudication engine 402. A medical claim 404 generated by the medical claim adjudication engine 402 may be transmitted at step 406 as adjudicated claim data (AJDCLM) or as an in initial accumulator record (ACCINT) to the system 100/data processing application 202. The system 100 and/or the data processing application 202 may generate accumulator records, for example, according to the methods described above in connection with FIGS. 3A-3B, and may transmit as update accumulator records (ACCUPD) to partnering claim adjudication engines that share accumulators. In FIG. 4A, a dental claim adjudication engine 408 and a vision claim adjudication engine 410 may each receive update accumulator records (ACCUPD) 412, 414, respectively, and each may acknowledge receipt of the update by transmitting an acknowledgement accumulator record (ACCACK) 416, 418, respectively. Optionally, the centralized accumulator 212/data processing application 202 may be required to transmit acknowledgements 420, 422 to the medical claim adjudication engine 402 upon the centralized accumulator 212/data processing application 202 receiving acknowledgements 416, 418 of the updates from the respective dental and vision claim adjudication systems 408, 410. In addition, the medical claim 404 generated by the medical claim adjudication engine 402 may optionally be transmitted to 424 and acknowledged by 426 other specialty systems 428 that share accumulators.

FIG. 4B illustrates another high level process flow 430 for the exchange of claim and accumulator records from a specialty benefit claims adjudication engine (e.g. vision and dental claim adjudication engines). In FIG. 4B, the process flow is for a vision claim 432 from the vision claim adjudication engine 410. The vision claim 432 may be transmitted as a post-adjudicated claim (ADJCLM) 434 to the system 100/data processing application 202, where the received claim data is processed into an initial accumulator record (ACCINT) and transmitted 436 to the medical claim adjudication engine 402. The medical claim adjudication engine 402 may generate an updated accumulator record (ACCUPD) after processing the initial accumulator record received from the centralized accumulator for the specialty benefit claim. In some implementations, the medical claim adjudication engine 402 may optionally transmit 438 an accumulator record and receive an acknowledgement 440 from other specialty claim adjudication engines 428. The medical claim adjudication engine 402 sends 442 the system 100/data processing application 202 a record containing the updated accumulator record (ACCUPD). The system 100/data processing application 202 then routes the updated accumulator record to the specialty benefit systems that share accumulators. For the dental system 408, the record is sent 444 as an update accumulator record (ACCUPD), whereas, for the vision system 410, the record is sent 446 as an acknowledgement record due to the vision system 410 generating the original vision claim 432 for the process flow 430. The vision and dental systems 410, 408, respectively, then send the system 100/data processing application 202 acknowledgement records (ACCACK) 448, 450. When required, upon receipt of acknowledgement records (ACCACK) 448, 450, the system 100/data processing application 202 sends acknowledgement records (ACCACK) 452, 454 to the medical claim adjudication engine 402. The process flow 430 may additionally be applicable to behavioral claims, according to the present disclosure.

FIG. 4C illustrates another high level process flow 460 for the exchange of claim and accumulator records from a prescription claims adjudication engine 462. In FIG. 4C, pharmacy claim 464 from the pharmacy claim adjudication engine 462 may be transmitted 466 first to the medical claim adjudication engine 402 where the received pharmacy claim data is processed into an initial accumulator record (ACCINT) and transmitted 468 to the medical claim adjudication engine 402. At step 470 and 472, the system 100/data processing application 202 sends a record containing the updated accumulator record (ACCUPD) to the dental claim adjudication engine 408 and the vision claim adjudication engine 410, respectively. The vision and dental systems 410, 408, respectively, then send the system 100/data processing application 202 acknowledgement records (ACCACK) 474, 476. When required, upon receipt of acknowledgement records (ACCACK) 474, 476, the system 100/data processing application 202 sends acknowledgement records (ACCACK) 478, 480 to the medical claim adjudication engine 402. In some implementations, the medical claim adjudication engine may optionally transmit 482 an accumulator record and receive an acknowledgement 484 from other specialty claim adjudication engines 428.

The technology described herein may be implemented as logical operations and/or modules in one or more systems. The logical operations may be implemented as a sequence of processor-implemented steps executing in one or more computer systems and as interconnected machine or circuit modules within one or more computer systems. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the invention. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A computer system for managing healthcare costs accumulated across a plurality of claims systems, the system comprising one or more computer processors performing the steps of:
   receiving claim data at an accumulator, the claim data for a plurality of members under a plurality of health plans;
   generating cost accumulator records using the claim data for each of the plurality of members, wherein the cost accumulator records comprise an accumulation of healthcare costs incurred;
   storing the cost accumulator records in an accumulator header table, wherein for each of the plurality of cost accumulator records stored in the accumulator header table, the accumulated costs are separated into cost accumulator records of a first type and cost accumulator records of a second type, wherein for each of the cost accumulator records of the first type and the second type, the accumulated costs incurred within a network for a health plan of a member are separated from the accumulated costs incurred outside of the network thereby generating four cost accumulator types including an in-network cost accumulator of the first type, an out-of-network cost accumulator of the first type, an in-network cost accumulator of the second type, and an out-of-network cost accumulator of the second type;
   validating the cost accumulator records by querying the accumulator header table based on a cost accumulator sub-type associated with each cost accumulator record; and
   receiving an acknowledgement from a plurality of receiving claim systems at the accumulator, the acknowledgement comprising a record of the receiving claim system's cost accumulator records for the plurality of the cost accumulator types routed.

2. The system of claim 1, wherein validating further comprises identifying a most recent record from a sequence of new records for processing.

3. The system of claim 1, wherein for each cost accumulator record, further comprising the step of retrieving a cross-reference for an original accumulator header record from the accumulator header table, the cross-reference linking the acknowledgement to the claim data.

4. The system of claim 1, wherein the one or more computer processors are further configured to determine whether each cost accumulator record contains a shared accumulator value of greater than zero.

5. The system of claim 4, wherein if the shared accumulator value is greater than zero, a routing message for the cost accumulator record is written.

6. The system of claim 5, wherein the routing message includes an originating claim adjudication engine identification information.

7. The system of claim 4, wherein if the shared accumulator value is not greater than zero, the one or more computer processors determines an input type for the cost accumulator record, the input type including a claim or an accumulator.

8. The system of claim 5, wherein the one or more computer processors are further configured to read the routing message and retrieve an accumulator record from the accumulator header table.

9. The system of claim 5, wherein the one or more computer processors are further configured to write and edit a working copy of the routing message.

10. The system of claim 1, further comprising receiving, at the accumulator, an update accumulator record or an acknowledgement accumulator record.

11. The system of claim 1, further comprising updating, via the accumulator, a plurality of accumulators across the plurality of claims systems.

12. The system of claim 1, wherein the plurality of claims systems comprise medical claims systems, dental claims systems, vision claims systems, pharmacy claims systems, behavioral claims systems, physical health claims systems, or combinations thereof.

13. The system of claim 1, wherein the one or more computer processors are further configured to deploy a common interface to each of the plurality of claims systems to facilitate communication with the accumulator.

14. The system of claim 1, wherein after receiving the claim data, the one or more computer processors are further configured to log key information embodied in the claim data.

15. The system of claim 1, wherein the claim data comprises adjudicated claim data or a received initial accumulator record for a plurality of adjudicated claims.

16. The system of claim 1, wherein the accumulator records of the first type are deductible cost accumulator records.

17. The system of claim 1, wherein the accumulator records of the second type are out-of-pocket cost accumulator records.

18. A computer system for managing healthcare costs accumulated across a plurality of claims systems, the system comprising one or more computer processors performing the steps of:
   receiving claim data at an accumulator, the claim data for a plurality of members under a plurality of health plans;
   generating cost accumulator records using the claim data for each of the plurality of members, wherein the cost accumulator records comprise an accumulation of healthcare costs incurred;
   storing the cost accumulator records in an accumulator header table, wherein for each of the plurality of cost accumulator records stored in the accumulator header table, the accumulated costs are separated into a plurality of types of cost accumulator records, wherein for each type of cost accumulator record, the accumulated costs incurred within a network for a health plan of a member are separated from the accumulated costs incurred outside of the network thereby generating at least four cost accumulator types including an in-network cost accumulator of a first type, an out-of-network cost accumulator of the first type, an in-network cost accumulator of a second type, and an out-of-network cost accumulator of the second type;

receiving an acknowledgement from a plurality of receiving claim systems at the accumulator, the acknowledgement comprising a record of the receiving claim system's cost accumulator records for the plurality of the cost accumulator types routed; and retrieving a cross-reference for an original accumulator header record from the accumulator header table, the cross-reference linking the acknowledgement to the claim data.

19. The system of claim 18, further comprising updating, via the accumulator, a plurality of accumulators across the plurality of claims systems.

20. The system of claim 18, wherein the claim data comprises adjudicated claim data or a received initial accumulator record for a plurality of adjudicated claims.

* * * * *